United States Patent [19]

Prakash

[11] Patent Number: 5,728,862

[45] Date of Patent: Mar. 17, 1998

[54] METHOD FOR PREPARING AND PURIFYING AN N-ALKYLATED ASPARTAME DERIVATIVE

[75] Inventor: Indra Prakash, Hoffman Estates, Ill.

[73] Assignee: The NutraSweet Company, Deerfield, Ill.

[21] Appl. No.: 790,113

[22] Filed: Jan. 29, 1997

[51] Int. Cl.⁶ .................................................. C07C 229/00
[52] U.S. Cl. ................................................. 560/40; 560/41
[58] Field of Search ................................. 560/40, 41

[56] References Cited

U.S. PATENT DOCUMENTS

| | | | |
|---|---|---|---|
| 5,480,668 | 1/1996 | Nofre et al. | 426/548 |
| 5,510,805 | 4/1996 | Claude et al. | 560/41 |

OTHER PUBLICATIONS

Addison Ault, "Techniques and Experiments for Organic Chemistry" 4th edition, pp. 105–113, 1983.

*Primary Examiner*—Samuel Barts
*Attorney, Agent, or Firm*—Fitzpatrick, Cella, Harper & Scinto

[57] ABSTRACT

A method is disclosed for preparing and purifying N-[N-(3,3-dimethylbutyl)-L-α-aspartyl]-L-phenylalanine 1-methyl ester from aspartame and 3,3-dimethylbutyraldehyde by hydrogenation in an organic solvent solution followed by the formation of an aqueous/organic solvent solution having an organic solvent content of about 17% to about 30% by weight of the aqueous/organic solvent solution.

21 Claims, No Drawings

METHOD FOR PREPARING AND PURIFYING AN N-ALKYLATED ASPARTAME DERIVATIVE

BACKGROUND OF THE INVENTION

1. Field of the Invention

This invention relates to an improved method of preparing and purifying an N-alkylated aspartame derivative which is particularly useful as a sweetening agent.

2. Related Background Art

It is known that various N-substituted derivatives of aspartame, such as disclosed in U.S. Pat. No. 5,480,668, are useful as sweetening agents. In particular, the N-alkylated aspartame derivative, N-[N-(3,3-dimethylbutyl)-L-α-aspartyl]-L-phenylalanine 1-methyl ester, is known as an extremely potent sweetening agent since its sweetening potency, on a weight basis, has been reported to be at least 50 times that of aspartame and about 10,000 times that of sucrose.

Since sweetening agents are mainly employed in foods for human consumption, it is extremely important that such sweetening agents be produced using methods which provide highly purified product. Such methods must also be commercially practicable, i.e., capable of use on an industrial scale and economically efficient.

U.S. Pat. No. 5,510,508 describes a method for preparing N-[N-(3,3-dimethylbutyl)-L-α-aspartyl]-L-phenylalanine 1-methyl ester of the formula

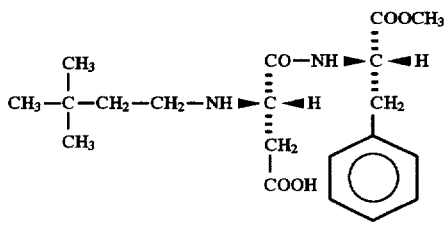

comprising treating an aqueous acetic acid/alcoholic solution of aspartame and 3,3-dimethylbutyraldehyde, at room temperature, with hydrogen at a pressure less than or equal to 1 bar (0.1 MPa) in the presence of a catalyst based on platinum or palladium. The product is purified by precipitation and filtration after the alcohol is removed from the solvent under vacuum.

There is, however, a need to prepare N-[N-(3,3-dimethylbutyl)-L-α-aspartyl]-L-phenylalanine 1-methyl ester of even greater purity than known in the art, particularly for use as a sweetening agent for human consumption.

SUMMARY OF THE INVENTION

This invention relates to a method for providing a highly purified N-alkylated aspartame derivative that may be used as a sweetening agent. In particular, the invention relates to a method for preparing N-[N-(3,3-dimethylbutyl)-L-α-aspartyl]-L-phenylalanine 1-methyl ester of the formula

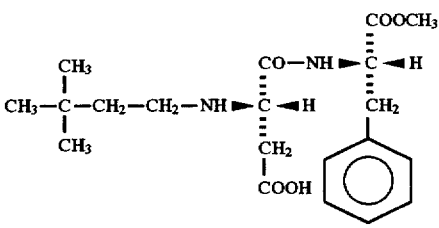

comprising the steps of (i) treating a mixture of aspartame and 3,3-dimethylbutyraldehyde in an organic solvent with hydrogen in the presence of a hydrogenation catalyst at a temperature and pressure effective to form an organic solvent solution of N-[N-(3,3-dimethylbutyl)-L-α-aspartyl]-L-phenylalanine 1-methyl ester; (ii) filtering the organic solvent solution to remove the hydrogenation catalyst; and (iii) forming an aqueous/organic solvent solution from the organic solvent solution to precipitate the N-[N-(3,3-dimethylbutyl)-L-α-aspartyl]-L-phenylalanine 1-methyl ester from the aqueous/organic solvent solution. Significantly, the aqueous/organic solvent solution has an amount of organic solvent of about 17% to about 30% by weight of the aqueous/organic solvent solution. A particularly preferred organic solvent for use in this method is methanol. The precipitate is recovered using standard filtration techniques to provide highly purified N-[N-3,3-dimethylbutyl)- L-α-aspartyl]-L-phenylalanine 1-methyl ester.

Another embodiment of this invention is directed to a method for purifying N-[N-(3,3-dimethylbutyl)-L-α-aspartyl]-L-phenylalanine 1-methyl ester comprising the steps of preparing an organic solvent solution of N-[N-(3,3-dimethylbutyl)-L-α-aspartyl]-L-phenylalanine 1-methyl ester and thereafter forming an aqueous/organic solvent solution from the organic solvent solution to precipitate the N-[N-(3,3-dimethylbutyl)-L-α-aspartyl]-L-phenylalanine 1-methyl ester from the aqueous/organic solvent solution. Again, the aqueous/organic solvent solution has an amount of organic solvent of about 17% to about 30% by weight of the aqueous/organic solvent solution. The purification method of this invention allows for the recovery of highly purified N-[N-3,3-dimethylbutyl)-L-α-aspartyl]-L-phenylalanine 1-methyl ester by filtration of the precipitate while the impurities remain in the aqueous/organic solvent solution.

DETAILED DESCRIPTION OF THE INVENTION

This invention is directed to an improved method of preparing and purifying an N-alkylated aspartame derivative, namely N-[N-(3,3-dimethylbutyl)-L-α-aspartyl]-L-phenylalanine 1-methyl ester. This N-alkylated aspartame derivative is a highly potent sweetening agent.

The N-[N-(3,3-dimethylbutyl)-L-α-aspartyl]-L-phenylalanine 1-methyl ester is prepared by first treating a mixture of aspartame and 3,3-dimethylbutyraldehyde in an organic solvent with hydrogen in presence of a hydrogenation catalyst. Aspartame and 3,3-dimethylbutyraldehyde are readily available starting materials, which are typically combined in a substantially equivalent molar ratio, e.g. about 1:1. Higher molar amounts of the aldehyde are more likely to lead to the generation of impurities, while excess molar amounts of aspartame are not preferred due to waste and cost.

The hydrogenation reaction is conducted in an organic solvent, preferably an alcohol and most preferably methanol.

If desired, water may be present in the reaction mixture so long as the organic solvent is present in an amount greater than about 30% by weight of the total weight of water and organic solvent. Essentially the concentration of organic solvent must be great enough to solubilize the N-[N-(3,3-dimethylbutyl)-L-α-aspartyl]-L-phenylalanine 1-methyl ester so as to avoid aggregation with the catalyst which is removed via filtration. Other exemplary organic solvents include tetrahydrofuran, ethyl acetate, and the like.

The hydrogenation catalyst may be selected from catalysts based on palladium or platinum such as for example, platinum on activated carbon, palladium on activated carbon, platinum black or palladium black. Other hydrogenation catalysts include, without limitation, nickel on silica, nickel on silica and alumina, Raney nickel, ruthenium black, ruthenium on carbon, palladium hydroxide on carbon, palladium oxide, rhodium black, rhodium on carbon and rhodium on alumina. The hydrogenation catalysts based on palladium or platinum are most preferred. The catalyst is present in an amount effective to produce the N-alkylated aspartame derivative in an acceptable yield. Generally, the weight ratio of catalyst to aspartame is about 0.01:1 to about 0.25:1, most preferably about 0.02:1.

The pH of the reaction mixture is typically between about 4.0 to about 6.5, most preferably about 5.0 to about 5.5. If desired, the pH of the reaction mixture can be adjusted by the addition of common acids or bases.

The components of the reaction mixture are hydrogenated in the presence of the hydrogenation catalyst under a hydrogen atmosphere. Typically the pressure of the hydrogen is held at about 5 psi to about 100 psi, most preferably about 30 psi to about 35 psi.

The hydrogenation reaction is conducted by first mixing the aspartame, and 3,3-dimethylbutyraldehyde, organic solvent, and catalyst to form a slurry, which is then hydrogenated at a temperature of about 20° C. to about 30° C., preferably about 22° C. to about 26° C. for approximately 2 to 48 hours, and most preferably for 12 to 16 hours.

The resulting organic solvent solution containing N-[N-(3,3-dimethylbutyl)-L-α-aspartyl]-L-phenylalanine 1-methyl ester is then filtered to remove the hydrogenation catalyst. Standard filtration techniques may be employed. Preferably a filtering aid, such as celite, is added and the solution is filtered with a sparkle filter.

After filtration, an aqueous/organic solvent solution having organic solvent in an amount of about 17% to 30% by weight of the aqueous/organic solvent solution is formed. The aqueous/organic solvent solution can be formed in any way that results in a solution having the above-described amount of organic solvent. For example, the organic solvent from the organic solvent solution containing N-[N-(3,3-dimethylbutyl)-L-α-aspartyl]-L-phenylalanine 1-methyl ester can be first reduced by, for example, rotary evaporation or distillation, and then replaced by water to achieve the desired organic solvent content. Or more preferably, after the water is added the organic solvent is further reduced by distillation to achieve the desired organic solvent content. It is also possible to add water to the organic solvent solution which is then reduced to achieve an organic solvent content of about 17% to about 30%, more preferably about 17% to about 25% by weight of the aqueous/organic solvent solution. Yet another possibility, if desired, is to add water and remove the organic solvent simultaneously. If the organic solvent is reduced to less than 17%, it is also possible to add back organic solvent to form an organic solvent solution having an organic solvent content between about 17 to about 30%.

After the aqueous/organic solvent solution having the specified organic solvent content is formed, the solution is held for about 2 to about 24 hours, most preferably at least about 12 hours and at a temperature of about 5°–25° C., most preferably about 10°–15° C. This hold period allows for substantial precipitation of the N-[N-(3,3-dimethylbutyl)-L-α-aspartyl]-L-phenylalanine 1-methyl ester which is then removed using standard filtration techniques.

The resulting filtrate, which may contain 10–15% of the N-alkylated aspartame derivative can be, if desired, recycled into the process. The recovered solid, which is preferably washed with water and then dried, is highly purified N-[N-(3,3-dimethylbutyl)-L-α-aspartyl]-L-phenylalanine 1-methyl ester.

As noted previously, another embodiment of this invention is directed to a method for purifying N-[N-(3,3-dimethylbutyl)-L-α-aspartyl]-L-phenylalanine 1-methyl ester, no matter how prepared. In this purification method the N-[N-(3,3-dimethylbutyl)-L-α-aspartyl]-L-phenylalanine 1-methyl ester may be formed in an organic solvent solution or added to organic solvent. As noted previously, the organic solvent solution may contain water as long as the N-[N-(3,3-dimethylbutyl)-L-α-aspartyl]-L-phenylalanine 1-methyl ester is solubilized in the organic solvent solution. The formation of the aqueous/organic solvent solution for this purification method is the same as previously described for the method of preparing N-[N-(3,3-dimethylbutyl)-L-α-aspartyl]-L-phenylalanine 1-methyl ester.

The Examples which follow are intended as an illustration of certain preferred embodiments of the invention, and no limitation of the invention is implied.

EXAMPLE 1

A slurry of α-aspartame a (29.43 g, 0.1 mol) and 3,3-dimethylbutyraldehyde (10 g, 0.1 mol) was formed in methanol (500 ml). To the slurry was added a palladium catalyst, Pd/C (4%, 50% wet, 1.2 g). The mixture was hydrogenated at 30 psi at room temperature for about 12 to 16 hours. The hydrogenated mixture was then filtered through a Celite bed and the bed was washed with methanol (50 ml). The methanol was reduced to about half the volume (250 ml) on a rotary evaporator under reduced pressure and then water (250 ml) was added to it. The remaining methanol was distilled to a level of about 17–25% methanol in the resulting aqueous/methanol solution. The aqueous/methanol solution was stirred at 10° to 15° C. for 2 to 12 hours. The precipitated solid was filtered, washed with water (50 ml) and dried in a vacuum oven at 40° C. (house vacuum) for 16 hours to yield 19.65–24.57 g of N-[N-(3,3 -dimethylbutyl)-L-α-aspartyl]-L-phenylalanine 1 -methyl ester (52–65%) as a white solid (>97% pure by HPLC).

COMPARATIVE EXAMPLE 1

Aspartame (50–60 g/L), 3,3-dimethylbutyraldehyde (20–30 g/L), methanol (30 ml) and a 0.1M aqueous solution of acetic acid (60 ml) were mixed with a palladium catalyst, Pd/C (10%; 1 g). The mixture was hydrogenated at 14.5 psi (0.1 MPa) at room temperature for about 2 hours. The methanol was then removed by evaporation and a white solid precipitate was recovered. The reaction was only 60–70% complete. After the product was filtered off, dried and washed with hexane, the resulting N-[N-(3,3-dimethylbutyl)-L-α aspartyl]-L-phenylalanine 1-methyl ester was found by HPLC to contain about 20 to 30% (0% of methanol) aspartame, 1 to 2% N,N-dineohexyl aspartame and 1–2% of a late eluter believed to be dineohexyl lactone. When the methanol level was distilled to a level of about 5–10% methanol in the resulting aqueous/methanol solution, the percentage of aspartame in the final isolated material went down to 3–5%.

EXAMPLE 2

N-[N-(3,3-dimethylbutyl)-L-α aspartyl]-L-phenylalanine 1-methylester was prepared in a manner similar to Comparative Example 1 with the exception that the methanol was not completely distilled off, but instead left at 20–24% by weight of the hydrogenated aqueous/methanol solution. The precipate was recovered by filtration, washed with water and dried. The resulting N-[N-(3,3-dimethylbutyl-L-aspartyl]-L-phenylalanine 1-methyl ester had a purity of >99% by HPLC.

Other variations and modifications of this invention will be obvious to those skilled in this art. This invention is not to be limited except as set forth in the following claims.

What is claimed is:

1. A method for purifying N-[N-(3,3-dimethylbutyl)-L-α-aspartyl]-L-phenylalanine 1-methyl ester of the formula

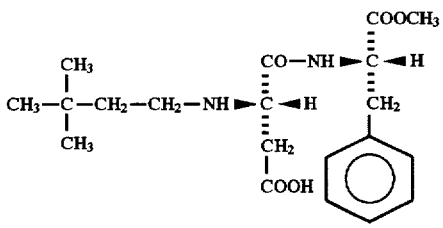

comprising the steps of:
(i) preparing an organic solvent solution of N-[N-(3,3-dimethylbutyl)-L-α-aspartyl]-L-phenylalanine 1-methyl ester and (ii) thereafter forming an aqueous/organic solvent solution from the organic solvent solution to precipitate the N-[N-(3,3-dimethylbutyl)-L-α-aspartyl]-L-phenylalanine 1-methyl ester from the aqueous/organic solvent solution, wherein said aqueous/organic solvent solution has an amount of organic solvent of about 17% to about 30% by weight of the aqueous/organic solvent solution, and wherein said organic solvent is methanol, tetrahydrofuran, or ethyl acetate.

2. The method according to claim 1, wherein said organic solvent is methanol.

3. The method according to claim 1, wherein the pH of the organic solvent solution is about 5.0 to about 5.5.

4. The method according to claim 2, further comprising the step of filtering the N-[N-(3,3-dimethylbutyl)-L-α-aspartyl]-L-phenylalanine 1-methyl ester precipitate from the aqueous/methanol solution.

5. The method according to claim 4, wherein the step of filtering the precipitate is conducted at least 12 hours after formation of the aqueous/methanol solution.

6. The method according to claim 5, wherein the aqueous methanol solution is held at a temperature in a range of 10° C. to 15° C. prior to the step of filtering the precipitate.

7. A method for preparing N-[N-(3,3-dimethylbutyl)-L-α-aspartyl]-L-phenylalanine 1-methyl ester of the formula

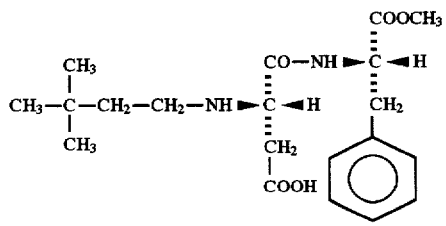

comprising the steps of (i) treating a mixture of aspartame and 3,3-dimethylbutyraldehyde in an organic solvent with hydrogen in the presence of a hydrogenation catalyst at a temperature and pressure effective to form an organic solvent solution of N-[N-(3,3-dimethylbutyl)-L-α-aspartyl]-L-phenylalanine 1-methyl ester; (ii) filtering the organic solvent solution to remove the hydrogenation catalyst; and (iii) forming an aqueous/organic solvent solution from the organic solvent solution to precipitate the N-[N-(3,3-dimethylbutyl)-L-α-aspartyl]-L-phenylalanine 1-methyl ester from the aqueous/organic solvent solution, wherein the aqueous/organic solvent solution has an amount of organic solvent of about 17% to about 30% by weight of the aqueous/organic solvent solution, and wherein said organic solvent is methanol, tetrahydrofuran, or ethyl acetate.

8. The method according to claim 7, wherein said organic solvent is methanol.

9. The method according to claim 7, wherein the pH of the organic solvent solution is about 5.0 to about 5.5.

10. The method according to claim 8, wherein the aspartame and 3,3-dimethylbutyraldehyde are present in a substantially equivalent molar ratio.

11. The method according to claim 10, wherein the hydrogenation catalyst is a palladium or platinum based catalyst.

12. The method according to claim 11, wherein a weight ratio of the hydrogenation catalyst to aspartame is about 0.02:1.

13. The method according to claim 8, wherein the pressure of the hydrogen is held at about 5 psi to about 100 psi.

14. The method according to claim 8, wherein the temperature is held between about 20° C. to about 30° C.

15. The method according to claim 8, wherein said aqueous/methanol solution contains methanol in an amount between about 17% to about 25% by weight of the aqueous/methanol solution.

16. The method according to claim 8, wherein said step of forming the aqueous/methanol solution comprises partially reducing the methanol content of the methanol solution, adding water and further reducing the methanol content to about 17% to about 25% by weight of the aqueous/methanol solution.

17. The method according to claim 8, wherein said step of forming the aqueous/methanol solution comprises adding water to the methanol solution followed by reducing the methanol content to about 17% to about 25% by weight of the aqueous/methanol solution.

18. The method according to any one of claims 15, 16 or 17 further comprising the step of filtering the N-[N-(3,3-dimethylbutyl)-L-α-aspartyl]-L-phenylalanine 1-methyl ester from the aqueous/methanol solution.

19. The method according to claim 18, wherein the step of filtering the precipitate is conducted at least 12 hours after the formation of the aqueous/methanol solution.

20. The method according to claim 19, wherein the aqueous methanol solution is held at a temperature in a range of 10° C. to 15° C. prior to the step of filtering the precipitate.

21. The method according to claim 19, wherein said precipitate is washed with water.

* * * * *

UNITED STATES PATENT AND TRADEMARK OFFICE
CERTIFICATE OF CORRECTION

PATENT NO. : 5,728,862

DATED : March 17, 1998

INVENTOR(S): INDRA PRAKASH

It is certified that error appears in the above-identified patent and that said Letters Patent is hereby corrected as shown below:

<u>TITLE PAGE</u>

Item: [56] "5,510,805" should read --5,510,508--.

Signed and Sealed this

Eleventh Day of May, 1999

Q. TODD DICKINSON

*Attest:*

*Attesting Officer*  *Acting Commissioner of Patents and Trademarks*